United States Patent [19]

LeTourneau et al.

[11] Patent Number: 4,745,222
[45] Date of Patent: May 17, 1988

[54] NOVEL ARYLOXYCYCLOALKANOLAMINOALKYLENE ARYL KETONES

[75] Inventors: Michael E. LeTourneau, Lebanon; James R. McCarthy, Zioneville; Donald L. Trepanier, Indianapolis, all of Ind.

[73] Assignee: Merrell Dow Pharmaceuticals Inc., Cincinnati, Ohio

[21] Appl. No.: 599,891

[22] Filed: Apr. 17, 1984

Related U.S. Application Data

[63] Continuation-in-part of Ser. No. 497,775, May 25, 1983, abandoned.

[51] Int. Cl.$^4$ .................. C07C 49/637; C07C 49/553
[52] U.S. Cl. ..................................... 564/305; 548/516; 548/455; 548/467; 548/336; 548/513; 548/374; 546/273

[58] Field of Search ................ 564/305; 548/516, 455, 548/467, 336, 513; 546/273; 568/374

[56] References Cited

U.S. PATENT DOCUMENTS

| | | | |
|---|---|---|---|
| 4,003,934 | 1/1977 | Grier et al. | 568/374 |
| 4,156,732 | 5/1979 | Long et al. | 549/57 |
| 4,431,843 | 2/1984 | Yoshida | 568/374 |
| 4,431,851 | 2/1984 | Moinet et al. | 564/305 |

Primary Examiner—John Kight
Assistant Examiner—M. L. Moore
Attorney, Agent, or Firm—John J. Kolano; Raymond A. McDonald

[57] ABSTRACT

This invention relates to aryloxycycloalkanolaminoalkylene aryl ketones to the processes for their preparation and to their use as antihypertensive agents.

17 Claims, No Drawings

NOVEL ARYLOXYCYCLOALKANOLAMINOALKYLENE ARYL KETONES

This application is a continuation-in-part application of our co-pending application Ser. No. 497,775, filed May 25, 1983 (now abandoned).

This invention relates to valuable therapeutically active chemical compositions belonging to the general class of aryloxycycloalkanolaminoalkylene aryl ketones, to the processes for making and using such compositions and to the chemical intermediates useful therefore. More specifically, this invention relates to the substituted aryloxycycloalkanolaminoalkyl aryl ketones described herein, to their use as antihypertensive agents, and to the processes and intermediates useful in the preparation thereof.

The aryloxy cycloalkanolaminoalkyl aryl ketones of this invention are compounds of the structural formula

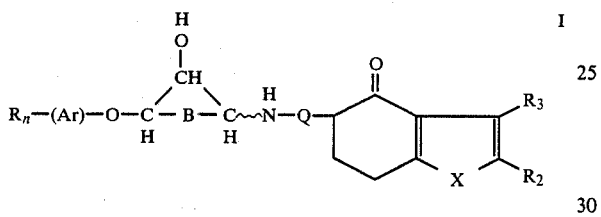

and the pharmaceutically acceptable salts thereof, wherein Ar represents phenyl, naphthyl, indolyl, thienyl and pyridyl, the R substituent attached to the aryl moiety (Ar) represents hydrogen, lower alkyl, halogeno, nitro, trifluoromethyl, trifluoromethoxy, methylene dioxy, lower alkanoyl, carboxy, hydroxy, lower alkoxy, cyano, —$SO_2NH_2$, lower alkylthio, $CH_3SO_2NH$—, amino, carboxamido, amidino and imidazol-2-yl; n represents 1, 2 or 3, B and Q each represent an alkylene bridge having 1 to 3 carbon atoms; X represents O, S, $NR_1$ or —CH=CH—, with $R_1$ being hydrogen or lower alkyl, $R_2$ and $R_3$ each being hydrogen, lower alkoxy, lower alkyl or phenyl; with the proviso that when X represents —CH=CH—, then the $R_2$ and $R_3$ groups are located at the 6- and 7-positions, respectively, of the resulting tetralone structure.

As used herein the term "alkylene" embraces those bridging moieties methylene (—$CH_2$—), ethylene (—$CH_2$—$CH_2$—) and propylene (—$CH_2$—$CH_2$—$CH_2$—). In the instance of "B", such alkylene moiety, together with the carbon atoms to which it is attached, forms a cycloalkanol moiety of the group cyclobutanol, cyclopentanol and cyclohexanol of which cyclopentanol is the most preferred. In the instance wherein Q represents an alkylene moiety, methylene is much preferred over the ethylene and propylene moieties. The term "lower alkyl" includes straight, branched chain and cyclic manifestations of saturated lower aliphatic hydrocarbyl radicals having 1 to 6 carbon atoms, of which methyl and ethyl are most preferred. Halogeno embraces all four members with chloro and fluoro being preferred. The term "lower" used to modify such terms as alkoxy, alkanoyl, alkylthio, alkylamino and the like embrace those moieties having up to six carbon atoms. The terms amino and carboxamido include their mono and di-alkyl manifestations thereof. The "Ar" aryl moiety includes pyridyl (including the 2-, 3-, and 4-position isomers thereof), indolyl includes those moieties attached through the oxygen bridging atom via a carbon atom of its benzenoidal moiety, particularly those prepared from the 4-hydroxy and 5-hydroxy indoles. Thienyl includes those attached to the oxygen atom at the 2- or 3-positions. The R substituents attached to the phenyl moiety are preferably located in the para position, although each of the ortho, meta or para positions may bear such substituents.

The aryl ketone moieties wherein "X" represents S, O, NR, or —CH=CH— are depicted by the formulae

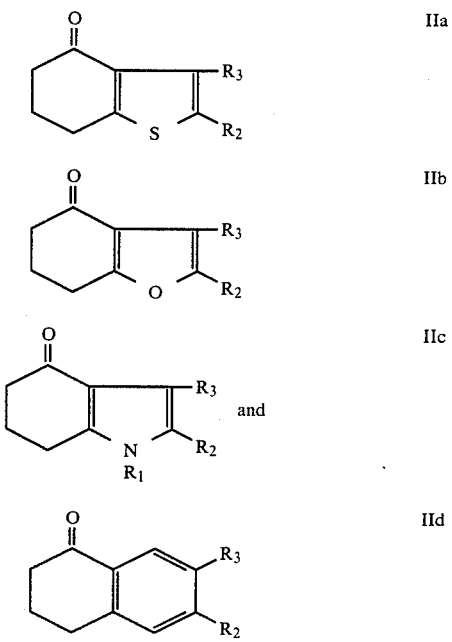

are 6,7-dihydrobenzo(b)thiophen-4-(5H)ones, 6,7-dihydro-4(5H)benzofuranones, 6,7-dihydro-1(H)indol-4(5H)ones, and 1-tetralones, respectively.

The term pharmaceutically acceptable salts thereof include those salts which are formed with various inorganic and organic acids. Such salts include HCl, HBr, $H_2SO_4$, $H_3PO_4$, methanesulfonic, toluensulfonic, maleic, fumaric, camphorsulfonic. The non-toxic physiologically acceptable salts are preferred, although other salts are also useful, e.g., in isolating or purifying the product.

The salts may be formed by conventional means, as by reacting the free base form of the product with one or more equivalents of the appropriate base or acid in a solvent or medium in which the salt is insoluble, or in a solvent such as water which is then removed in vacuo or by freeze-drying or by exchanging the anions of an existing salt for another anion on a suitable ion exchange resin.

The cycloalkanol moieties of the compounds of formula I contain three (3) asymmetric carbon atoms which lead to four (4) steroisomeric forms, i.e., cis-cis, trans-trans, cis-trans and trans-cis. In the generic scope of this invention all such forms are contemplated and thus, in the depiction of formula I, the chemical bonds of the relevant asymmetric centers are depicted as wavy lines to indicate either an alpha or beta configuration. In their use as antihypertensive agents, it is generally preferred that the nitrogen atom be in the alpha configuration when attached to the cycloalkanol moiety of the compounds embraced by formula I, and that the aryloxy moiety be in the beta configuration. The hydroxy moiety may be in either configuration. For convenience, however, unless it is necessary for a specific aspect of the teachings for this invention, the isomersm will be ignored and, as for formula I, the customary wavy lines will be used to designate the embracement of both the alpha and beta configurations.

In general, the preparation of the compounds of formula I is readily achieved by standard chemical reactions analogously known in the art. In essence, the preparation of the compounds of formula I can be effected by the condensation of an appropriately substituted α-methylene ketone (IV) with a substituted aryloxycycloalkanolamine (III) by contacting equimolar quantities of the reactants together in an inert solvent. Although the reaction mixture may be warmed to shorten the reaction time, temperatures of 50° C. or less are more desirable with room temperature being preferred. The reaction is generally fairly rapid but can be left over several days if desired. In practice, any alcohol in which the amine reactant is soluble would be suitable, although ethanol, under neutral conditions, is preferred. Other classes of solvents such as those represented by acetonitrile and ethyl acetate are also useful. The product may be isolated as the free base or as an acid addition salt, such as, for example its hydrochloride salt.

The foregoing reaction may be schematically depicted as follows:

REACTION SCHEME A

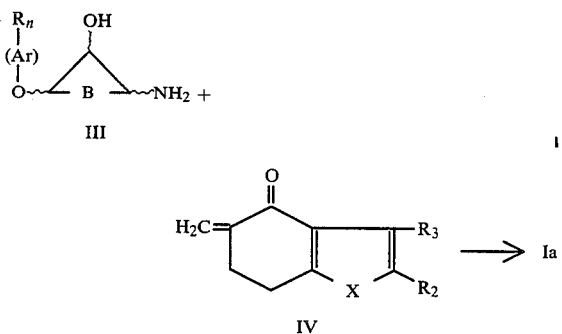

wherein $R_n$, (Ar), B, X, $R_2$ and $R_3$ are as previously defined, Ia being those compounds of formula I except wherein Q is other than methylene.

Quite obviously it is not necessary to effect the foregoing condensation reaction with the R substituent(s) already attached to the aryloxycycloalkanolamine. If desired chemical modification on the aryl moiety can be effected after the condensation of the enone and the amine in order to achieve greater efficiency. For example, the cyano moiety may be converted to a carboxyl moiety by hydrolyzing the nitrile with 6N hydrochloric acid, sulfuric or other mineral acid under standard conditions such as by heating under reflux temperatures for about 12-24 hours. The carboxyl moiety may be converted to an alkoxy carbonyl by the standard Fisher esterification procedure such as by heating the carboxy-containing compounds with an appropriate alcohol in the presence of an acid, e.g., hydrogen chloride. The carboxamido-containing compounds may be obtained by heating the esters in the presence of ammonia, or any appropriate alkyl amine, preferably in a pressure bomb at about 100°-150° C. in an inert solvent, e.g., benzene, toluene and the like. Alternatively, the carboxamido moiety may be prepared by hydrolyzing a nitrile function with concentrated sulfuric by heating on a steam bath at temperatures of about 50°-100° C.

In those instances wherein $R_n$ is imidazol-2-yl, the compounds are prepared by a condensation reaction wherein the nitrile (i.e., $R_n$ is cyano) is heated with ethylene diamine at about 150°-200° C. for about 2 hours. The amidino compounds are prepared from the corresponding nitriles wherein the nitrile is converted to an imino ether which is then treated with ammonia in alcohol at temperatures of about 0° C. to room temperature. Of course, in those instances wherein the chemical conversions for the preparation of the various $R_n$ groups takes place after the enone-amine condensation (Reaction Scheme A), reactive nitrogen atoms (e.g., the unsubstituted nitrogen atom of the indole moiety or of the 6,7-dihydro1(H)indol-4(5H)ones moiety) must be protected prior to these chemical modifications, preferably using benzyl, tosyl, or trimethylsilyl protecting groups. The N-protected compounds, are readily prepared and removed by standard techniques.

The preparation of the required aryloxycycloalkanolamine reactants (III) are prepared by standard techniques analogously known in the art. In general, either an aryloxycycloalkene is oxidized to yield a 2,3-epoxide of the aryloxycycloalkene or a 2-cycloalkenol is converted to the corresponding epoxide of an aryloxycycloalkanol. The epoxides are then converted to aryloxy epoxides and then to the corresponding α-azido-5-aryloxycycloalkanol which azides are then chemically reduced to the desired amine.

In effecting the foregoing epoxidations, the usual oxidizing agents such as 3-chloroperbenzoic acid, per acetic acid and the like may be reacted with the appropriate cycloalkene according to standard techniques known in the art. The azides may be formed by reaction of the epoxides with sodium azide by heating the reactants at reflux temperatures, under a nitrogen atmosphere, utilizing inerts solvents such as ethanol. Using thin layer chromatography techniques, the reaction is monitored and upon completion the reaction is quenched. The resulting azides are hydrogenated under pressure, using palladium on carbon as a catalyst, to reduce it to the corresponding amine.

As indicated above, the three asymmetric carbon atoms of the substituted cycloalkanolamine moiety of the compounds of formula I give rise to a multiplicity of isomeric forms which effect subtle differences in their end-use characteristics as anti-hypertensive agents. Thus, it is preferable to utilize discriminating techniques in the preparation of the substituted aryloxycycloalkanolamine reactants to ensure the obtention of the desired isomers.

The preparation of the (1α,2β,5β)-2-amino-5-aryloxycyclopentanols may readily be accomplished from an appropriate R-substituted aryloxy cyclopentene by a series of reactions and techniques analogously known for achieving similar effects. Reaction of the cyclopentene (V) with 3-chloroperbenzoic acid (3-CPA) or 40% peracetic acid and the like yields a mixture of trans and cis epoxides (VIa and VIb respectively) are separated by standard partition techniques much as, for example, a Waters Prep HPLC system 500 using commercially available silica cartridges. The desired trans-epoxide (i.e., trans-2-aryloxy-6-oxabicyclo(3.1.0)hexane (VIa)) is preferably opened by reaction with sodium azide to form a (1α,2β,5β)-2-azido-5-aryloxycycloalkanol which is then chemically reduced to form the desired (α,β,β) stereoisomer. Standard reduction techniques, such as for example, catalytic (Pd/C) hydrogenation, may conveniently be utilized. The foregoing sequences may be schematically depicted by reaction scheme B, as follows:

REACTION SCHEME B

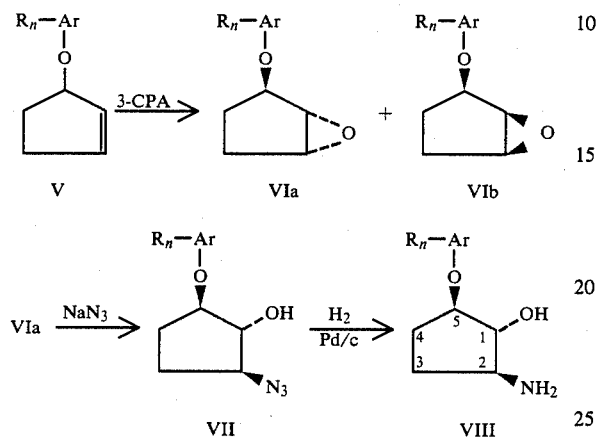

wherein R and Ar are as defined for formula I. It is to be noted that the numbering of the cycloalkanolamine reactants (IV) starts with the carbon atom bearing the hydroxy moiety and proceeds in a clockwise fashion. The numbering of that moiety following condensation with an enone (IV) starts with the carbon atom bearing the nitrogen atom and then proceeds in a direction opposite than that for the reactant.

Alternatively, the preparation of the (1β,2β,5α)-2-amino-5-aryloxycyclopentanols entails the reaction of trans-6-oxabicyclo(3.1.0)cyclohexan-2-ol with triphenylphosphine and an $R_n$-substituted hydroxyaryl (e.g., phenol) in the presence of an azodicarboxylate to yield the cis-epoxide (VIb). This epoxide is then subjected to treatment with sodium azide and the resulting 2 azido compound is chemically reduced to the desired amine according to the techniques described above. Preferably, the reaction on the trans-epoxy alcohol is effected in the presence of a dialkylazodicarboxylate in an inert solvent such as benzene or tetrahydrofuran. Purification of the desired product can be achieved by column chromatography on silica gel using chloroform. Similarly, the trans epoxide may be made starting with the cis-epoxy alcohol and by following the same technique there is produced the desired compound (VIa) in a stereospecific form.

The preparation of the (1β,2β,5β)-2-amino-5-aryloxycyclopentanols can be readily effected by an anchimerically assisted inversion of the hydroxy group of a (1α,2β,5β)-2-amino-5-aryloxycyclopentanol by treating an amide thereof with thionyl chloride to form an oxazoline which is hydrolized with a strong protic acid, e.g., hydrochloric acid. A desired amide is the p-nitrobenzamide which is formed by reacting the cyclopentylamine with p-nitrobenzyl chloride in the presence of triethylamine in an inert solvent such as tetrahydrofuran.

The preparation of the (1α,2α,5β)-2-amino-5-aryloxycyclopentanols conveniently start by epoxidizing an amidocyclopentene, e.g., acetamido or benzamido cyclopentene with 3-chloroperbenzoic acid followed by treatment with a hydroxy aryl (e.g., phenol, naphthol, hydroxy indole, hydroxy thiophene or pyridinol) anion which opens up the epoxide to yield a (1α,2α,5β)-N-(2-hydroxy-3-aryloxycyclopentyl) amide. The amide is then treated with a strong base or strong acid to give the free amine.

The foregoing procedures yield the four stereoisomeric forms of the 2-amino-5-aryloxycyclopentanols which, for clarity, are depicted as follows:

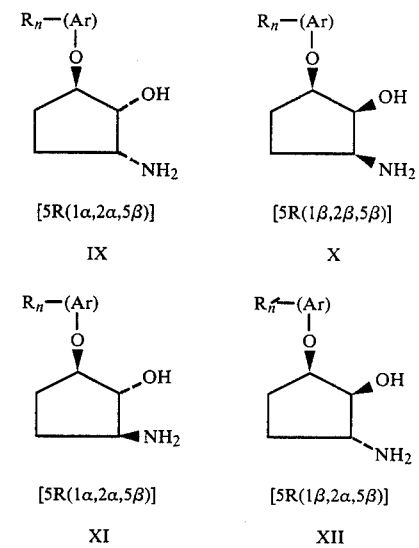

wherein $R_n$ and Ar are as previously defined.

It is understood, of course, that each of the foregoing stereospecific isomers exits as racemates of their individual enantiomers even though, for convenience, the compounds are depicted in their 5R-enantiomeric form. (N.B. The 5S-enantiomer of the compound of formula IX would be [5S-(1β,2β,5α)]. Mixtures may readily be separated according to standard techniques such as separation of mixtures with optically active acids, by the use of prep columns such as Prep Percol column, or, in the alternative the individual enantiomorphs may be prepared with an enantiospecific synthesis such as by epoxidizing the olefin with an enantioselective agent.

The preparation of the exocyclic methylene ketones (IV) required for the condensation reaction with the 2-amino-cycloalkanols (III) is readily achieved by standard techniques analogously known for achieving such reactions. In general, the formation of the α-methylene group is readily prepared by conducting a Mannich reaction upon the cyclic ketone wherein the ketone is first converted to a dialkylaminomethyl intermediate in situ and then is converted to the 2-methylene. In those instances wherein X represents nitrogen, it is preferred to protect the nitrogen atom of the pyrrole ring with an N-protecting group such by reaction with tosyl chloride. It is also possible to prepare an anion at the 5-position adjacent the carbonyl group and the so-formed anion is heated with ethyl formate and then condensed with the amine (III) by reductive amination procedures using sodium cyanoborohydride or other reagents known in the art. Alternatively, use of Pd/C may be used.

In those instances wherein Q is other than a methylene bridge standard techniques are again utilized to form the reactants to condense with the aryloxycycloalkanolamines. To synthesize compounds wherein Q represents an ethylene bridge the ketones (IIa-d) are treated with lithium diisopropylamine (LDA) in tetrahydrofuran to form an anion at the carbon atom adjacent the carbonyl, which anion is then treated with ethylene oxide to form a hydroxyethyl group. This group is then oxidized to the aldehyde by treatment with a Collins reagent. To synthesize those reactants wherein Q represents a propylene bridge, the ketones (IIa-d) are similarly treated with LDA to form an anion which anion is treated with acrolien (i.e., $CH_2=CH-CHO$) to form the corresponding aldehyde. In each instance the so-formed aldehyde is subjected to a reductive amination by reacting the aldehyde and the cycloalkanolamine in the presence of sodium cyanoborohydride.

The following examples typify the preferred methods of synthesis of the compounds of this invention.

Preparation of Intermediate
2-Amino-5-Aryloxycycloalkanols

EXAMPLE 1

(1α,2β,5β)-2-Amino-5-Phenoxycyclopentanol

Step A

Trans-2-Phenoxy-6-oxabicyclo(3.1.0)hexane

In a 3-neck 2L-flask with overhead stirrer and thermometer was added 3-phenoxycyclopentene (40 g, 0.25 mol) and $CH_2Cl_2$ (250 ml). The solution was cooled to 4° C. and a solution of ca. 85% 3-chloroperbenzoic acid (86 g) in $CH_2Cl_2$ (750 ml) was added dropwise. The reaction was stirred for 15 hours, slowly warming to room temperature. The mixture was cooled in an ice bath and the precipitate was collected by filtration and washed with cold $CH_2Cl_2$ (75 ml). The light yellow filtrate was washed with an aq. sol. (500 ml) of $Na_2SO_3$ (60 g), ice cold 1N NaOH (2×250 ml) and brine (100 ml). The colorless organic layer was dried ($Na_2SO_4$) and evaporated to an oil (41.8 g). The light yellow oil was dissolved in 150 ml of $CH_2Cl_2$:hexane (1:1) and purified on a Waters Prep LC/system 500 using two Prep PAK ™ 500/silica cartridges. Seven injections were made and the two major peaks (which had baseline separation) were collected. Integration of the peaks indicated a 74:26 ratio of the two epoxides. The first and second components from the seven runs were combined into two fractions and evaporated. The first fraction on evaporation yielded 25 g of the desired epoxide, $^1$H NMR ($CDCl_3$) 1.5-2.2 (m, 4, $CH_2CH_2$), 3.55 (s, 2, C1-H, C5-H), 4.75 (d, 1, J=3, C2-H), 6.65-7.4 (m, 5, Ar). (The second fraction yields the same product as that produced by Step A of Example 4.)

Step B (1α,2β,5β)-2-Azido-5-phenoxycyclopentanol

Trans-2-phenoxy-6-oxabicyclo-(3.1.0)hexane (10 g, 0.057 mol) was dissolved in ethanol (100 ml). Sodium azide (10 g, 0.154 mol) and ammonium chloride (1.37 g, 0.025 mol) were dissolved in warm water (25 ml) and this solution was added to the ethanol solution. The reaction was refluxed under $N_2$ and was monitored by TLC (SS2). After refluxing for 16 hours, the reaction was diluted with brine and extracted with $CH_2Cl_2$ (3×100 ml). The combined organic layers were washed with brine (100 ml), dried ($Na_2SO_4$) and evaporated to a yellow oil (12.4 g, 100%). TLC showed one sopt with a lower $R_f$ than the product of step A. The oil was dissolved in a small volume of $CH_2Cl_2$ and filtered through a column of silica gel (75 g) using the same solvent. The fraction (ca. 600 ml) containing product was evaporated to a colorless oil (10.8 g, 87%): IR (thin film) 3375 (br) and 2100 (s) cm$^{-1}$: the azide was used immediately for the preparation of the amines below.

Step C (1α,2β,5β)-2-Amino-5-Phenoxycyclopentanol Hydrochloride

The hydroxy azide of step B (10.8 g, 0.049 mol) was dissolved in ethanol (150 ml), 5% Pd/C (1 g) and conc. hydrochloric acid (10 ml) were added. The mixture was hydrogenated at 55 psi for 16 hours. The catalyst was removed by filtration and the filtrate was evaporated to a white solid. The solid was recrystallized from isopropyl alcohol yielding analytically pure product (7.55 g, 67%): mp 213°-5° C.; $^1$H NMR (DMSO-d$_6$) 1.45-2.45 (m, 4, $CH_2CH_2$), 3.3 (m, 1, C2-H), 4.15 (m, 1, C1-H), 4.5 (m, 1, C5-H), 5.9 (m, 1, OH, exchangable), 6.7-7.45 (5, m, Ar), 8.5 (br s, 2, $NH_2$).

Step D (1α,2β,5β)-2-Amino-5-phenoxycyclopentanol

The hydroxy azide of step B was hydrogenated as in the preparation of step C with the exclusion of HCl yielding the amine which crystalizes from water: mp 99-100C,; $^1$H NMR (CDCL$_3$-DMSO-d$_6$-D$_2$O) 1.2-2.2 (m, 4 $CH_2CH_2$), 3.0 (dd, 1, $J_{2,1}=7$, J=14, C2-H), 3.75 (dd, 1, $J_{1,2}=7$, $J_{1,5}=5$, C1H), 4.4 (m, 1, C5-H), 6.65-7.4 (m, 5, Ar).

EXAMPLE 2

(1β,2β,5β)-2-Amino-5-Phenoxycyclopentanol

Step A (1β,2α,3β)-N-(2-Hydroxy-3-phenoxycyclopentyl)-p-nitrobenzamide

To a solution of the cyclopentylamine of step D, Example 1, (3.86 g, 0.02 mol) in THF (75 ml), triethylamine (2.02 g, 0.02 mol) and ether (75 ml) was added a solution of p-nitrobenzoyl chloride (3.72 g, 0.02 mol) in THF:ether (1:1) (25 ml) all at once. After 10 min., the white precipitate (5.6 g) containing the product of this step and Et$_3$N.HCl was removed by filtration and washed with ether. The filtrate was evaporated to dryness in vacuo and the resulting solid was triturated with ether and collected by filtration (3.5 g). The original 5.6 of material was added to water (100 ml), stirred for 15 min., collected by filtration and combined with the second 3.5 g crop of product. Recrystallization of the combined product from ethanol gave analytically pure product of this step. (5.15 g, 75%): mp 204°-206° C.; IR (Nujol) 3310, 1640, 1600, 1550, 1520, cm$^{-1}$; $^1$H NMR (CDCl$_3$-DMSO-d$_6$) 1.6-2.5 (m, 4, $CH_2CH_2$), 4.2 (m, 2, C1-H and C2-H, 4.58 (m, 1, C3-H), 5.25 (d, 1, J=3, OH), 6.7-7.5 (m, 5, Ar), 8.22 (AB quartet, 4, J=9.5, 4-NO$_2$-Ar).

Step B 2-(4-Nitrophenyl)-(β)-6-phenoxy-1-aza-3-oxobicyclo[3.2.0]oct-2-ene hydrochloride To a dry 2 neck-15 ml round bottom with stirring bar, $N_2$ bubbler and thermometer was added the p-nitrobenzoylamide from Step A (1.0 g, 2.9 m-mol) and SOCl$_2$ (10 ml) (freshly distilled from P(0φ)$_3$). The light yellow solution was heated at 40° (inside temp) and the progress of the reaction was monitored by NMR. TMS was added to a small aliquot of the reaction solution and the position and coupling of the cyclopentyl hydrogen on the phenoxy carbon was monitored. This hydrogen at 5 min. reaction time was observed as a clean d of d at δ 5.5 which became a multiplet at δ 5.8 after 2 hours. In addition the p-nitrobenzoyl AB quartet shifted from δ 8.0 to 8.4 after 2 hours. The reaction was poured into anhyd ether (125 ml) under $N_2$ with overhead stirring. After 30 minutes, the fine light yellow precipitate was collected on a sintered glass funnel and washed with ether (0.85 g, 80%): mp 138°–40° C.; IR (Nujol) 2350 (br), 1655, 1600, 1590, 1535, 1460, 1390 cm$^{-1}$, mass spec (CI) m/e 325 (m+1).

Step C (1β,2β,5β)-2-Amino-5-phenoxycyclopentanol hydrochloride

The oxazoline of step B (3.9 g, 10.8 m-mol) was treated at reflux with glyme: 5N HCl (25 ml: 75 ml) for 24 hours. The reaction was cooled in an ice bath and the white solid, mp 235°–238° C. (p-nitrobenzoic acid, as determined by TLC) (1.7 g, 95% was removed by filtration and washed with a small volume of water. The filtrate was evaporated in vacuo to a light pink crystalline solid. The crystals of the desired product were triturated with ether and collected by filtration (2.1 g, 85%): mp 214°–216° C. Recrystallization from isopropanol (ca. 75 ml) gave analytically pure material mp 216°–217° C.

Step D

The free base could be obtained by dissolving the product of Step C in water at room temperature (ca. 1 g/10 ml) and basifying the solution with 5N NaOH. The solution was cooled in an ice bath and the resulting crystals were collected by filtration and recrystallized from toluene: mp 94°–96° C.; $^1$H NMR (CDCl$_3$) 1.88 (m, 4, CH$_2$CH$_2$), 2.4 (m, 3, NH$_2$ and OH), 3.2 (m, 1, C2-H), 3.98 (m, 1, C1-H), 4.5 (dd, 1, J~5, J~9, C5-H), 6.7–7.4 (m, 5, Ar).

EXAMPLE 3

(1α,2α,5β)-2-Amino-5-Phenoxypentanol HCl

Step A

Cis-N-6-Oxabicyclo(3.1.0)hex-2-ylacetamide

3-Acetamidocyclopentene (120 g, 0.06 mol) was treated with 3-chloroperbenzoic acid (215 g) by the procedure of Vince and Daluge (*J. Med. Chem.*, 17, 578 (1974)) to yield 84 g of the desired product, mp 92.5°–93° C.

Step B (1α,2α,3β)-N-(2-Hydroxy-3-phenoxycyclopentyl)acetamide

In a 250 ml 3-neck round-bottom flask fitted with a N$_2$ inlet valve, condenser and addition funnel was placed NaH (1.7 g, 0.071 mol) and dry DMF (30 ml). To this suspension was added a solution of phenol (13.0 g, 0.138 mol) in DMF (50 ml) dropwise. After the reaction subsided, a solution of cis-N-6-oxabicyclo(3.1.0)hex-2-ylacetamide (10 g, 0.071 mol) in DMF (45 ml) was added and the reaction was heated at 145°–150° C. (inside temp). The reaction was followed by G. C. (200° C., SE-52 column) or $^1$H NMR (small aliquot of reaction diluted with brine and extracted into CDCl$_3$). Disappearance of the singlet at δ 3.55 from epoxide indicates complete reaction). After 2.5 hours, the reaction was added to ice water (ca. 400 ml) and the mixture was extracted with ethyl acetate (5×150 ml). The combined extracts were washed thoroughly with brine, dried (Na$_2$SO$_4$) and evaporated to an oil. The oil was triturated with ether to induce crystallization and cyclohexane was added to complete crystallization. The crystalline product was collected by filtration and air dried to give 9.6 g of the desired product, mp. 123°–125.5° C. after recrystallization from ethyl acetate or acetonitrile.

Step C (1α,2α,5β)-2-Amino-5-phenoxycyclopentanol hydrochloride and the free base A 9.5 g (0.04 mol) quantity of the acetamide of Step B, methanol (125 ml) and 3N HCl (125 ml) was heated at reflux for 15 hours under a N$_2$ atmosphere. The solution was concentrated in vacuo to afford a slurry of crystalline product. The crystals were collected by filtration, washed with a small volume of ethanol and dried in vacuo to give 7.5 g (81%) of the amine hydrochloride salt, mp 215°–217° C. A small sample was recrystallized from i-PrOH for analysis: mp 215°–217° C.; The free base was isolated from the hydrochloride by partitioning the hydrochloride between ether (150 ml) and 1M K$_2$CO$_3$(75 ml) and evaporating the ether layer to obtain white crystals: mp 90°–91° C.

EXAMPLE 4

(1β,2α,5β)-2-Amino-5-phenoxycyclopentanol

Step A

Cis-2-Phenoxy-6-oxabicyclo(3.1.0)hexane

Phenol (7.05 g) (37.5 mmoles), triphenylphosphine (7.85 g) (30 mmoles) and (1β,2α,5β)-6-oxabicyclo(3.1.0)-cyclohexan-2-ol (2.5 g) (25 mmoles) were combined under N$_2$ at room temperature. Diisopropyl azodicarboxylate (DIAD) (6.05 g) (30 mmoles), is mixed with an equal volume of THF and added dropwise to an ice cooled bath of the reaction mixture. The reaction was allowed to stir at room temperature for 24 hours. 30% H$_2$O$_2$ (3.5 ml) was added and the reaction was diluted with 100 ml of toluene and washed with 20% sodium thiosulfate (100 ml), 1N NaOH (2×50 ml), brine (100 ml), dried (Na$_2$SO$_4$) and evaporated to a white solid in vacuo. Kugelrohr distillation at 100° to 115° (0.1 mm) yielded two fractions of white crystalline solid (2.8 g and 3.5 gm respectively). Tlc (CHCl$_3$) shows a slow moving impurity. The pot residue contains no product as determined by tlc (CHCl$_3$). The combined distilled products were extracted with hot hexane (2×100 ml) leaving an insol. non-UV absorbing residue. Evaporation of the solution left a white crystalline solid (4.2 g 95%). This material can be purified by column chromatography on silica gel (Merck) using CHCl$_3$ or can be carried on to the cis-trans amino alcohol before elimination of any impurities.

Step B (1β,2α,5β)-2-Azido-5-phenoxycyclopentanol

The cis-epoxide of Step A (3.5 g, 0.02 mol) was dissolved in ethanol (50 ml). Sodium azide (3.5 g, 0.054 mol) and ammonium chloride (0.48 g, 0.009 mol) were dissolved in warm water (8 ml) and this solution was added to the ethanol solution. The reaction was heated at reflux under a nitrogen atmosphere and the progress of the reaction was monitored by tlc (SS2). After 16 hours, the reaction was diluted with CHCl$_3$ (150 ml) and brine (100 ml). The aqueous layer was extracted with additional CHCl$_3$ (50 ml). The combined organic layers were washed with brine, dried (Na$_2$SO$_4$) and evaporated in vacuo, affording 3.7 g (85%) of the desired product as a clear yellow oil, homogenous by tlc, which was used in the next experiment without further purification.

Step C (1β,2α,5β)-2-Amino-5-phenoxycyclopentanol hydrochloride

To a solution of the azide of Step B (4.1 g, 0.019 ml) in ethanol (100 ml) was added conc. hydrochloric acid (5 ml) and 5% Pd-C (0.5 g). The mixture was shaken with hydrogen at 55 psi for 24 hours. Tlc indicated complete reduction of the azide. The reaction was filtered through a Celite pad and the catalyst was thoroughly washed with hot ethanol. The filtrate was concentrated in vacuo to give a highly crystalline while solid. Recrystallization from ethanol gave the desired product mp 233°–234.5°.

Step D (1β,2α,5β)-2-Amino-5-phenoxycyclopentanol

The azide of Step B (9.3 g, 0.042 mol), 5% Pd/C (900 mg) and ethanol (150 ml) were combined in a Parr bottle and hydrogenated at 50 psi. After 6 hours, tlc (SS2) indicated complete reduction. The reaction mixture was filtered through a celite pad and the filtrate was evaporated in vacuo to a white solid recrystallized from water (ca. 80 ml), and the resulting white needles (5.6 g, 68%) of the desired product were collected by filtration, mp. 123°–125°.

In a similar manner by altering the reactants and by substantially following the foregoing procedures (with obvious modifications flowing from the change in the reactants) there also may be produced the (1α2β,5β) and the (1β,2β,5β), (1α,2α,5β) and (1β,2α,5β) isomeric forms thereof of the following compounds:
2-amino-5(1-naphthoxy)cyclopentanol,
2-amino-5-(2-naphthoxy)cyclopentanol,
2-amino-5(4-indolinyloxy)cyclopentanol,
2-amino-5(5-indolinyloxy)cyclopentanol,
2-amino-5(2-thienyloxy)cyclopentanol,
2-amino-5(3-thienyloxy)cyclopentanol,
2-amino-5(4-sulfonamidophenoxy)cyclopentanol,
2-amino-5(3-methylsulfonamidophenoxy)cyclopentanol,
2-amino-5(4-pyridinyloxy)cyclopentanol,
2-amino-5(3-pyridinyloxy)cyclopentanol,
2-amino-5(2-pyridinyloxy)cyclopentanol,
2-amino-5(2-methylphenoxy)cyclopentanol,
2-amino-5(3-methylphenoxy)cyclopentanol,
2-amino-5(4-methylphenoxyl)cyclopentanol,
2-amino-5(4-methoxyphenoxy)cyclopentanol,
2-amino-5(4-chlorophenoxy)cyclopentanol,
2-amino-5(3,4-dimethoxyphenoxy)cyclopentanol,
2-amino-5(2-fluorophenoxy)cyclopentanol,
2-amino-5(2,3-dimethylphenoxy)cyclopentanol,
2-amino-5(2-ethylphenoxy)cyclopentanol,
2-amino-5(2-methyl-4-chlorophenoxy)cyclopentanol,
2-amino-5(4-nitrophenoxy)cyclopentanol,
2-amino-5(4-cyanophenoxyl)cyclopentanol,
2-amino-5-(4-hydroxyphenoxy)cyclopentanol,
2-amino-5(4-trifluoromethylphenoxy)cyclopentanol,
2-amino-5(4-trifluoromethoxyphenoxy)cyclopentanol,
2-amino-5(4-acetylphenoxy)cyclopentanol,
2-amino-5(4-methylthiophenoxy)cyclopentanol,
2-amino-5(4-carboxyphenoxy)cyclopentanol,
and the like.

EXAMPLE 5

(1α,2α,4β)-2-Amino-4-phenoxy cyclobutanol

Step A 2-(Dibenzylamino)-4-bromocyclobutanone HBr 2-(Dibenzylamino)cyclobutanone is dissolved in CHCl$_3$ (1 molar conc.) and treated dropwise with one equivalent of bromine dissolved in CHCl$_3$ (1 molar conc.) at 0° C. After stirring the mixture for 30 minutes, evaporate the solution to obtain the desired product of this step.

Step B 2-(Dibenzylamino)-4-phenoxy cyclobutanone

The hydrobromide salt of Step A is partitioned between CHCl$_3$ and saturated NaHCO$_3$ and the organic layer dried (Na$_2$SO$_4$) and then evaporated to an oil. The oil is dissolved in DMF (1 mol.) and treated with 2 equivalents of sodium phenoxide in DMF (1 mol) on a steam bath for 6 hours. The mixture is cooled to room temperature, diluted with brine and extracted with ether (4×100 ml). The combined organic layer is washed with brine, dried (MgSO$_4$) and evaporated to an oil; the product of this step.

Step C (1α,2α,4β)-2-Amino-4-phenoxycyclobutanol

The product of Step B is dissolved in ethanol (1M) containing 1 equivalent of hydrochloric acid. 10% Pd/C is added (10% by wt. of the cyclobutanone) and the mixture is hydrogenated in a Parr bottle at 60 p.s.i. for 15 hours. Filter off the catalyst and evaporate the filtrate. The resulting residue is partitioned between saturated aqueous NaHCO$_3$ and ethyl acetate. The organic layer is dried (Na$_2$SO$_4$), evaporated to a solid in vacuo and purified by flash chromatography using chloroform:methanol:conc. ammonium hydroxide (75:10:1) yielding the desired product of this example.

In a similar manner by altering the reactants and by substantially following the foregoing procedure the 2-amino-4-(substituted phenoxy)cyclobutanol analogs, (such as those enumerated after Example 4) may also be produced.

EXAMPLE 6

6,7-Dihydro-2-Methylbenzo(b)thiophene-4(5-methylene)(5H)-one.

Step A

3-Hydroxy-2-(2-oxopropyl)-2-cyclohexen-1-one

To a slurry of powdered K$_2$CO$_3$ (4.34 Kg, 31.4 moles) in chloroform (8.5 l), 1,3-cyclohexanedione (3.5 Kg, 31.2 moles) was added with stirring. To this mixture, at an ice-bath temperature, chloroacetone (2.9 Kg, 28.2 moles based on 90% purity) was added over a 1 hour period under a N$_2$ atmosphere with stirring. The reaction temperature was raised slowly to room temperature and it was then allowed to stay at room temperature for 3 days. As the reaction proceeded, stirring became more and more difficult. Distilled water (2 l)

was added slowly and the mixture was then transferred to an aqueous sodium hydroxide solution (1 1 50% NaOH to 6 l H₂O) with stirring. Additional water (1 l) and chloroform (1 l) were used to rinse the remainer of the mixture from the reaction flask. The pH of the solution was less than 10 and additional sodium hydroxide (1 l of 50% solution) was added to bring the pH of the solution to approx. 10. After stirring for 20 minutes, the mixture was allowed to settle and the organic layer was separated. The aqueous layer was acidified with conc. hydrochloric acid solution (15 lb) and then ethyl acetate (9 l) was added. The mixture was stirred for 20 minutes, allowed to settle, and the organic layer was separated. This organic layer was washed with brine (2 l), dried over Na₂SO₄, and the filtrate was concentrated under reduced pressure to yield a brown oily product (approx. 4.5 l ). This material can be crystallized from ether, but may be used directly in the next step without further purification, mp 80°–81° C. (crystals obtained from ether crystallization).

Step B 6,7-Dihydro-2-methylbenzo(b)thiophen-4(5H)-one

The crude product obtained above (approx. 4.5 l of brown oil material) was dissolved in absolute ethanol (11 l). To this solution 2,2-dimethoxypropane (275 g) and methanesulfonic acid (500 g) were added and the solution was then vigorously purged with N₂ gas with stirring for 20 minutes. Hydrogen sulfide gas was passed through the solution at a good rate for 1.0 hour with stirring and the reaction mixture was allowed to stand at room temperature for 20 hours. Additional hydrogen sulfide gas was passed through the solution for 30 minutes at a moderate rate with good stirring. After 3 days at room temperature, additional hydrogen sulfide gas was passed through the solution for 20 minutes at a moderate rate with stirring. After 2 days, N₂ gas was passed through the solution with stirring for 40 hours to purge the excess hydrogen sulfide gas. Sodium hydroxide solution (50% NaOH, 1350 g) was added slowly with stirring. During the addition the temperature rose to 45° C. After stirring for 1 hour, most of the solvent was removed under reduced pressure. Extraction was performed with methylene chloride (16 l) and water (15 l). After stirring for 30 minutes, the mixture was allowed to settle and the organic layer was removed and washed with aqueous sodium hydroxide solution (1350 g of 50% NaOH + 18 l of H₂O). The organic layer was filtered through celite to remove some emulsion materials. The filtered organic solution was washed with water (2 × 14 l), dried over MgSO₄, filtered and the filtrate was concentrated under reduced pressure to give a brown oily product. This material can be be distilled (90°–125°/0.3 mmHg) if desired, but may be used directly in the next step without purification.

Step C 6,7-Dihydro-5-dimethylaminomethyl-2-methylbenzo(b)thiophene-4(5H)one.

To 22 l reactor, thiopheneketone of Step B (1992 g, 12 moles), aqueous formalin (1272 g, 36–38% solution), dimethylamine hydrochloride (1078 g, 13.22 moles) and conc. HCl (25 g) were added and the mixture was stirred under a N₂ atmosphere and then warmed to 60° C. over a 1.5 hour period. The reaction mixture was then further warmed to 85°–90° C. over a 1.5 hour period and then finally heated at 93°–95° C. for 3.5 hours. The reaction mixture was stored overnight during which time it slowly cooled to room temperature. It was then heated at 90° C. for an additional one hour and then cooled to 25° C. To the reaction mixture water (2.4 l), CH₂Cl₂ (3.6 l) and then aqueous NaOH solution (1080 g of 50% NaOH in 1.2 l of H₂O) were added slowly with stirring. This mixture was transferred to a 50 liter reactor to separate the phases and the original reactor was washed with 1 l of water and 1 l of CH₂Cl₂ which were combined with previous transferred mixture. The organic layer was separated and the aqueous layer was washed with 1 l of CH₂Cl₂. The combined organic layer was washed with water (2 × 1.5 l) and used directly in the next step.

Step D 6,7-Dihydro-2-methyl-5-methylenebenzo(b)thiophene-4(5H)-one

Method A

The organic solution obtained from Step C was charged into a 22 liter reactor and to this solution CH₂Cl₂ (2 l) and K₂CO₃ (1790 g) were added with stirring. Methyliodide (2.28 kg) was added slowly to this mixture over a 1.5 hour period at 15° to 25° C. The temperature of this exothermic reaction was controlled by using an ice-bath. During the addition of CH₃I, a white solid material precipitated from the solution. At this stage, the majority of the reaction mixture is a quarternary ammonium salt. To the reaction mixture water (220 g) was added slowly which caused a slightly exothermic reaction to occur, but the temperature of the reaction mixture did not exceed 25° C. The reaction mixture was stirred at room temperature for 60 hours under a N₂ atm. To the reaction mixture, water (30 liters) and CH₂Cl₂ (2 liters) were added. The mixture was a thick slurry which made phase separation very difficult. It was warmed to 35° C. which allowed the organic phase to be separated. The aqueous layer was extracted with CH₂Cl₂ (1.5 liters) at 35° C. and the organic layer was separated. The combined organic layer was dried over MgSO₄, filtered and the filtrate was concentrated under reduced pressure to give the crude product (2.13 kg) as an oil. (This material was used directly in the next coupling reaction).

Method B

A premixed solution of dimethylamine hydrochloride (44.9 g, 0.55 moles) and aqueous formaldehyde (37% solution 53 g, 0.65 moles) was added to thiopheneketone (83 g, 0.5 moles) at room temperature followed by conc. HCl (1 g). This mixture was heated with stirring at 98° C. The initially two-phase system became homogeneous after 20 mins. and after 2.5 hours, the mixture was cooled slightly and sodium acetate trihydrate (27.7 g, 0.2 moles) was added followed by heating at 80° C. for 2 hours. The reaction was worked up by adding water (200 ml) and methylene chloride (300 ml) followed by phase separation. The aqueous layer was washed with CH₂Cl₂ (2 × 100 ml) and the combined organic layer was washed with dil. HCl and water. The organic layer was then dried over MgSO₄, filtered and the filtrate was concentrated to afford the desired α-methylene ketone of this example, an amber oily product.

Similarly, by altering the reactants and by substantially following the foregoing procedures (with obvious modifications flowing from the nature of the reactants) there may also be produced the following compounds:

6,7-dihydro-2,3-dimethyl-5-methylenebenzo(b)thiophene-4(5H)-one;
6,7-dihydro-2,3-dimethoxy-5-methylenebenzo(b)thiophene-4(5H)-one;
6,7-dihydro-2-methoxy-5-methylenebenzo(b)thiophene-4(5H)-one;
6,7-dihydro-3-methoxy-5-methylenebenzo(b)thiophene-4(5H)-one;
6,7-dihydro-2-phenyl-5-methylenebenzo(b)thiophene-4(5H)-one;
6,7-dihydro-3-methyl-5-methylenebenzo(b)thiophene-4(5H)-one;
and the like.

EXAMPLE 7

6,7-Dihydro-2-methyl-5-methylenebenzo(b)furan-4-(5H)-one

Step A 6,7-Dihydro-2-methylbenzo(b)furan-4(5H)-one

To a solution of conc. H$_2$SO$_4$ (300 ml) cooled in an ice-bath was added a solution of 3-hydroxy-2(2-oxopropyl)-2-cyclohexene-1-one (190 g in 300 ml CH$_2$Cl$_2$). Upon completion of addition, the mixture was stirred at ambient temperature for about 1 hour. The mixture was then slowly poured into 3 l ice water, and then about 1 l of CH$_2$Cl$_2$ was added. The layers are separated and the aqueous layer extracted thrice with CH$_2$Cl$_2$ and the combined CH$_2$Cl$_2$ layers again extracted thrice with water. The CH$_2$Cl$_2$ layer washed thrice with dilute aqueous NaHCO$_3$, then once with water and dried (MgSO$_4$). Concentration in vacuo afford an orange oil.

Step B

To a solution of the furanone of Step A (164.5 g/1.10 mole) in about 400 ml THF was added, in four separate portions, N-methylanilium trifluoroacetate (TAMA) (243 g) and trioxymethylene (99 g) over 3½ hours, and the mixture refluxed for 20 hours. The mixture was cooled and partitioned between Et$_2$O and water, the layers separated and the aqueous layer was extracted twice with Et$_2$O. The combined Et$_2$O layers were washed exhaustively with water, with NaHCO$_3$ and then with brine, dried over MgSO$_4$ and conc. in vacuo to yield an amber oil. This oil was flash chromatographed on silica gel using CH$_2$Cl$_2$ as solvent in several runs of 10–20 g per run. Fractions containing the fast moving material were combined, concentrated in vacuo to obtain the desired product as a yellow oil.

In a similar manner by using the techniques of the foregoing example there may be produced:
6,7-dihydro-2,3-dimethyl-5-methylenebenzo(b)furan-4(5H)-one,
6,7-dihydro-2-ethyl-5-methylenebenzo(b)furan-4(5H)-one,
6,7-dihydro-2-benzyl-5-methylenebenzo(b)furan-4-(5H)-one,
6,7-dihydro-2-phenyl-5-methylenebenzo(b)furan-4(5H)-one,
6,7-dihydro-2-methoxy-5-methylenebenzo(b)furan-4-(5H)-one,
6,7-dihydro-2,3-dimethoxy-5-methylenebenzo(b)furan-4(5H)-one.

EXAMPLE 8

6,7-Dihydro-2-methyl-5-methylene-1-tosyl-1(H)-indol-4(5H)-one

STEP A 6,7-Dihydro-2-methyl-1(H)-indol-4(5H)-one

To a solution of 3-hydroxy-2(2-oxopropyl)-2-cyclohexen-1-one (150 g, 0.89 moles) in ethanol (900 ml), ammonium acetate (75 g, 0.97 moles) was added and the mixture was stirred at room temperature for 2 days. The precipitated solid material was filtered and dried to give 70 g of the desired indolone. The filtrate was concentrated under reduced pressure to approx. ¼ of the original volume and the residue was cooled which afforded a 2nd crop of the desired material (26 g). The filtrate was again concentrated and cooled to obtain a 3rd crop as impure precipitated solids. To the filtrate, 50% NaOH (100 g) in water (50 ml) was added and the mixture was cooled to obtain a 4th crop as impure precipitated solids. The 3rd and 4th crops were combined and crystallized from ethanol-water which provided the pure desired product, mp. 204°–205° C.

Step B 6,7-Dihydro-2-methyl-1-tosyl-1(H)indol-4(5H)-one

To a solution of the above indolone (110 g, 0.70 moles) in anhydrous DMF (1 liter, dried over 3 A molecular sieve) at ice-bath temperature, 50% NaH (50 g, 0.83 moles) was added slowly with stirring. When the addition was complete, the mixture was stirred at room temperature for 30 min. The solution was cooled in an ice-bath and was slowly added to a solution of tosyl-chloride (140 g, 0.73 moles) in CH$_2$Cl$_2$ (400 ml) over a 30 min. period with stirring. The ice-bath was removed and the reaction mixture was stirred at room temperature for 2 hours. Acetic acid (approx. 10 ml) was added to the reaction mixture to destroy the excess NaH. The mixture was concentrated under reduced pressure using a vacuum pump. Water (250 ml) and ether (250 ml) were added to the concentrated residue and the mixture was stirred for 30 minutes. The precipitated solid was filtered and triturated with small amounts of ethyl acetate and ether to remove colored materials. The filtered white solid material was dried to afford the desired tosyl compound, mp. 152°–154° C.

Step C (Method A)

A mixture of N-tosylindolone of Step B (200 g, 0.643 moles), paraformaldehyde (60 g, 2 moles) and N-methylanilinium trifluoroacetate (100 g, 0.45 moles) in anhydrous THF (700 ml) was heated at reflux for 3.5 hours. At this point, hplc showed a 50:50 ratio of starting material and product. Additional paraformaldehyde (30 g, 1 mole) and N-methylanilinium trifluoroacetate (50 g, 0.23 moles) were added and the reaction mixture was heated at reflux for 9 hours to yield a 12:85 ratio of starting material and product (from hplc). An additional 2 hours at reflux did not change the ratio. Therefore, additional paraformaldehyde (15 g) and N-methylanilinium trifluoroacetate (25 g) were added and the mixture was heated at reflux for 5 hours. Finally, one more addition of paraformaldehyde (15 g) and N-methylanilinium trifluoroacetate (25 g) was made and the reaction mixture was heated at reflux for 5 hours to give a 6:90 ratio of starting material/product. The reaction mixture was concentrated under reduced pressure and extraction was performed using ethyl acetate (1 liter) and aqueous HCl solution. The organic layer was washed with aqueous HCl solution (at this time, the phase separation was not clear, and it was filtered through Celite), water and aqueous NaHCO$_3$ solution. The organic layer was dried over MgSO$_4$, filtered and the filtrate was concentrated under reduced pressure to obtain a light colored solid material. This solid material was triturated with ether and filtered. After drying, 130 g (0.39 moles, contaminated approx. 3% by starting material. The desired α-methylene ketone was obtained in approx. 60% yield, mp. 129°–131° C.

(Method B)

A mixture of N-tosylindolone (4 g), dimethylamine hydrochloride (1.16 ), aqueous formalin (1.36 g, 36–38% solution) and a few drops of conc. HCl in DME (4 ml) was heated at reflux for 6 hours. Additional dimethylamine hydrochloride (250 mg), aqueous formalin (270 mg) and a drop of conc. HCl were added and the mixture was heated at reflux for 3 hours to obtain a mixture. To this mixture, NaOAc.3H$_2$O (500 mg) was added and the reaction mixture was heated at reflux for 1.5 hours. Extraction was performed using water and ethylacetate and the organic layer was washed with water followed by aqueous NaHCO$_3$ solution. After drying and concentrating the organic layer, the residual solid material was triturated with ether to afford the desired product (less pure than the compound obtained from method A).

Similarly, by altering the reactants and by substantially following the procedures of this example there produced the following compounds:

6,7-dihydro-2,3-dimethyl-5-methylene-1-tosyl-1(H)-indol-4(5H)one,
6,7-dihydro-2,3-dimethoxy-5-methylene-1-tosyl-1(H)-indol-4(5H)one,
6,7-dihydro-3-methoxy-5-methylene-1-tosyl-1(H)-indol-4(5H)one,
6,7-dihydro-5-methylene-2-phenyl-1-tosyl-1(H)-indol-4(5H)one.

EXAMPLE 9

2-Methylene-1-tetralone

To a solution of 1-tetralone (164.5 g) in about 400 ml THF was added, in four separate portions, TAMA (243 g) and trioxymethylene (99 g) over 3½ hours, and the mixture refluxed for 20 hours. The mixture was cooled and portioned between Et$_2$O and water, the layers separated and the aqueous layer extracted twice with Et$_2$O. The combined Et$_2$O layers are exhaustively washed with water, NaHCO$_3$ and then with brine, dried (MgSO$_4$) concentrated in vacuo to yield an oil which is flash chromatographed on silica gel using CH$_2$Cl$_2$ in several runs of 10–20 g per run. Fractions containing the fast moving material are combined, concentrated in vacuo to obtain the desired 2-methylene-1-tetralone.

In a similar manner by using the techniques of the foregoing example there may be produced the following compounds:
2-methylene-6-methyl-1-tetralone,
6,7-dimethyl-2-methylene-1-tetralone,
6,7-dimethoxy-2-methylene-1-tetralone,
2-methylene-6-phenyl-1-tetralone.

Preparation of Final Products

EXAMPLE 10

(1α,2α,3β)-6,7-Dihydro-5-(((2-hydroxy-3-phenoxycyclopentyl)amino)methyl)-2-methyl-1H-indol-4(5H)-one hydrochloride A mixture of the α-methyleneketone of method A, Step C, Example 8 (140 g contaminated in approx. 3%) and (1β,2β,5α)-2-amino-5-phenoxycyclopentanol (81 g) in ethylacetate (50 ml) was heated at reflux for 3 hours. An equilibrium state was reached within an hour at this temperature to give a 25:77 ratio of starting material and product, since the reaction did not proceed further after the first hour of the 3 hour reaction period. The reaction mixture was left at room temperature for one day to obtain 13:73 ratio of starting material and product. To this mixture, 45 g of conc. HCl was added and the mixture was heated at reflux for 20 min. After standing overnight at room temperature, the precipitated hydrogen chloride salt was filtered to yield 200 g of the N-tosyl intermediate. A 190 g portion of this coupled hydrogen chloride salt was dissolved in aqueous sodium hydroxide (300 ml of 50% NaOH in 200 ml H$_2$O) and methanol (1.9 liters) by heating. The reaction mixture was left at room temperature overnight and it was concentrated under reduced pressure to remove most of the methanol. The product was extracted with ethyl acetate (1 liter), and the ethyl acetate solution was washed with water (300 ml), dried over Na$_2$SO$_4$, filtered and the filtrate was concentrated under reduced pressure to afford a very viscous material. This material was dissolved in ethyl alcohol (500 ml) and conc. HCl (50 ml) was added slowly with stirring. The precipitated solid was filtered and dried to obtain 80 g of product as a 1st crop. HPLC analysis of this 1st crop showed a 34:63 diastereomeric ratio and the mother liquor was greatly enriched in the other diastereomer. An additional 20 g of the desired product was obtained from the mother liquor and the combined solid (100 g) was digested in ethanol (50 ml) and ethyl acetate (400 ml). The precipitated solid was filtered and dried to afford 92 g of the desired product in a 46.54 ratio of diastereomers, mp. 219°–222° C.

In a similar manner, by changing the 2-aminocyclopentanol reactant and by substantially following the procedure of the foregoing example there are produced the [1α,2α,3β], [1β,2α,3β], [1α,2β,3β] and [1β,2β,3β] isomeric forms of the following compounds:
6,7-dihydro-5-(((2-hydroxy-3-(1-naphthoxy)cyclopentyl)amino)methyl)-2-methyl-1H-indol-4(5H)one HCl;
6,7-dihydro-5-(((2-hydroxy-3-(2-naphthoxy)cyclopentyl)amino)methyl)-2-methyl-1H-indol-4(5H)one HCl;
6,7-dihydro-5-(((2-hydroxy-3-(4-indolinyloxy)cyclopentyl)amino)methyl)-2-methyl-1H-indol-4(5H)one HCl;
6,7-dihydro-5-(((2-hydroxy-3-(5-indolinyloxy)cyclopentyl)amino)methyl)-2-methyl-1H-indol-4(5H)one HCl;
6,7-dihydro-5-(((2-hydroxy-3-(2-thienyloxy)cyclopentyl)amino)methyl)-2-methyl-1H-indol-4(5H)one HCl;
6,7-dihydro-5-(((2-hydroxy-3-(3-thienyloxy)cyclopentyl)amino)methyl)-2-methyl-1H-indol-4(5H)one HCl;
6,7-dihydro-5-(((2-hydroxy-3-(4-sulfonamidophenoxy)cyclopentyl)amino)methyl)-2-methyl-1H-indol-4(5H)one HCL;

6,7-dihydro-5-(((2-hydroxy-3-(3-methylsulfonamido-phenoxy)cyclopentyl)amino)methyl)-2-methyl-1H-indol-4(5H)one HCl;

6,7-dihydro-5-(((2-hydroxy-3-(4-pyridinyloxy)cyclopentyl)amino)methyl)-2-methyl-1H-indol-4(5H)one HCl;

6,7-dihydro-5-(((2-hydroxy-3-(2-methoxyphenoxy)cyclopentyl)amino)methyl)-2-methyl-1H-indol-4(5H)one HCl;

6,7-dihydro-5-(((2-hydroxy-3-(3-methylphenoxy)cyclopentyl)amino)methyl)-2-methyl-1H-indol-4(5H)one HCl;

6,7-dihydro-5-(((2-hydroxy-3-(4-methylphenoxy)cyclopentyl)amino)methyl)-2-methyl-1H-indol-4(5H)one HCl;

6,7-dihydro-5-(((2-hydroxy-3-(4-methoxyphenoxy)cyclopentyl)amino)methyl)-2-methyl-1H-indol-4(5H)one HCl;

6,7-dihydroxy-5-(((2-hydroxy-3-(4-chlorophenoxy)cyclopentyl)amino)methyl)-2-methyl-1H-indol-4(5H)one HCl;

6,7-dihydro-5-(((2-hydroxy-3-(3,4-dimethoxyphenoxy)cyclopentyl)amino)methyl)-2-methyl-1H-indol-4(5H)one HCl;

6,7-dihydro-5-(((2-hydroxy-3-(2-fluorophenoxy)cyclopentyl)amino)methyl)-2-methyl-1H-indol-4(5H)one HCl;

6,7-dihydro-5-(((2-hydroxy-3-(2,3-dimethylphenoxy)cyclopentyl)amino)methyl)-2-methyl-1H-indol-4(5H)one HCl;

6,7-dihydro-5-(((2-hydroxy-3-(2-ethylphenoxy)cyclopentyl)amino)methyl)-2-methyl-1H-indol-4(5H)one HCl;

6,7-dihydro-5-(((2-hydroxy-3-(2-methyl-4-chlorophenoxy)cyclopentyl)amino)methyl)-2-methyl-1H-indol-4(5H)one HCl;

6,7-dihydro-5-(((2-hydroxy-3-(4-nitrophenoxy)cyclopentyl)amino)methyl)-2-methyl-1H-indol-4(5H)one HCl;

6,7-dihydro-5-(((2-hydroxy-3-(4-cyanophenoxy)cyclopentyl)amino)methyl)-2-methyl-1H-indol-4(5H)one HCl;

6,7-dihydro-5-(((2-hydroxy-3-(4-hydroxyphenoxy)cyclopentyl)amino)methyl)-2-methyl-1H-indol-4(5H)one HCl;

6,7-dihydro-5-(((2-hydroxy-3-(4-trifluoromethylphenoxy)cyclopentyl)amino)methyl)-2-methyl-1H-indol-4(5H)one HCl;

6,7-dihydro-5-(((2-hydroxy-3-(4-trifluoromethoxyphenoxy)cyclopentyl)amino)methyl)-2-methyl-1H-indol-4(5H)one HCl;

6,7-dihydro-5-(((2-hydroxy-3-(4-acetylphenoxy)cyclopentyl)amino)methyl)-2-methyl-1H-indol-4(5H)one HCl;

6,7-dihydro-5-(((2-hydroxy-3-(4-methylthiophenoxy)cyclopentyl)amino)methyl)-2-methyl-1H-indol-4(5H)one HCl;

6,7-dihydro-5-(((2-hydroxy-3-(4-carboxyphenoxy)cyclopentyl)amino)methyl)-2-methyl-1H-indol-4(5H)one HCl;
and the like.

EXAMPLE 11

[(1α,2α,3β)]6,7-Dihydro-5-(((2-hydroxy-3-phenoxycyclopentyl)-amino)methyl)-2-methylbenzo(b)thiophen-4(5H)-one hydrochloride (1α,2α,5β)-2-Amino-5-phenoxycyclopentanol (1.97 g) was dissolved in absolute ethanol (57 ml) at 50° C. with stirring. To this solution thiophene-α-methylene ketone of Example 6, Step D, (1.86 g), was added slowly with stirring at 30°-40° C. The reaction mixture was stirred at room temperature under a $N_2$ atmosphere for 3 hours. During this time, a white solid material precipitated. The reaction was allowed to stand at room temperature overnight. The precipitated solid material was filtered. The solid material was recrystallized from ethyl acetate which produced the desired free base. The material was dissolved in ethyl acetate and the solution is treated with ethanolic HCl. The hydrochloride salt immediately precipitated, m.p. 184°-187° C.

EXAMPLE 12

(1β,2α,3β)-6,7-Dihydro-5-(((2-hydroxy-3-phenoxycyclopentyl)amino)methyl)-2-methylbenzo(b)thiophen-4(5H)-one HCl The amine hydrochloride salt of Example 1 (2.3 g, 0.01 mol) was dissolved in water (ca. 35 ml) and basified with 5N NaOH. The resulting white crystalline solid was extracted into ethyl acetate (4×35 ml, 2 ml of isopropanol added to first extraction). The combined organic layers were dried ($Na_2SO_4$) and evaporated to a white solid. The solid was dissolved in ethanol (70 ml) and the methylene ketone of Example 6, Step D (2.2 g, 0.011 mol, ca 90% pure) was added. The reaction was left at room temp for 60 hours and the resulting white crystals were collected by filtration (1.15 g) mp 138°-146°. The crystals were dissolved in ethanolic HCl and evaporated in vacuo to a white solid that was triturated with $CH_3CN$ and collected by filtration. The product was crystallized from ethanol yielding analytically pure material, mp. 188°-189.5° C.

EXAMPLE 13

(1α,2β,3β)-6,7-Dihydro-5-(((2-hydroxy-3-phenoxycyclopentyl)amino)methyl)-2-methybenzo(b)thiophen-4(5H)-one A 1.25 g (5.44 mmol) quantity of the (1β,2α,5β) amine hydrochloride of Example 4, 1 ml of ethanol, and 10 ml of $H_2O$ were had stirred and 1N NaOH was added until the slurry was strongly basic. The well stirred slurry was vacuum filtered and the white solid was washed with a small quantity of water. Air-drying afforded 1.0 g of the amine, which was dissolved in 30 ml of ethanol. To this ethanolic solution, swirled by hand, was added 1.2 g (ca. 6.06 mmol) of the enone of Example 6 (ca. 90% purity). The reaction was allowed to stand over the week-end. The reaction was filtered (gravity) and the filtrate was treated with ethanolic HCl; 20 ml of ether was added and the solution was placed under a nitrogen stream. The crystals which formed were vacuum filtered, washed with a small quantity of ethanol, and dried (vacuum) to afford 1.25 g of the desired hydrochloride salt, mp. 198°-200° C.

EXAMPLE 14

(1β,2β,3β)-6,7-Dihydro-5-(((2-hydroxy-3-phenoxycyclopentyl)amino)methyl)-2-methylbenzo(b)thiophen-4(5H)-one To a solution of the all cis amine of Example 2 (6.0 g, 0.03 mol) in ethanol (75 ml) was added the exocyclic methylene ketone from Example 6, Step D (6.0 g, ca. 90% pure, 0.03 mol). The light yellow solution was left at room temp overnight, acidified with ethanolic HCl and evaporated to a foam in vacuo (oil pump, bath temp <40°). The foam was dissolved in CH₃CN and allowed to stand at room temp. After 1 hour the resulting white crystalline solid of unreacted cis-amine (3.0 g) was collected by filtration. The filtrate yielded off-white crystals after standing at room temp. overnight. The product was recrystallized from ethanol (18 ml) yielding product, mp. 194°–195° C.

In a similar manner, by changing the 2-aminocyclopentanol reactants of examples 11–14 with the isomeric forms of those listed compounds following Example 4 and by substantially following the procedures of the foregoing 11–14 examples there are produced the corresponding (1α,2α,3β), (1β,2α,3β), (1α,2β,3β) and (1β,2β,3β) isomeric forms of the following compounds:

6,7-dihydro-5-(((2-hydroxy-3-(1-naphthoxy)cyclopentyl)amino)methyl)-2-methylbenzo(b)thiophen-4(5H)one HCl;
6,7-dihydro-5-(((2-hydroxy-3-(2-naphthoxy)cyclopentyl)amino)methyl)-2-methylbenzo(b)thiophen-4(5H)one HCl;
6,7-dihydro-5-(((2-hydroxy-3-(4-indolinyloxy)cyclopentyl)amino)methyl)-2-methylbenzo(b)thiophen-4(5H)one HCl;
6,7-dihydro-5-(((2-hydroxy-3-(5-indolinyloxy)cyclopentyl)amino)methyl)-2-methylbenzo(b)thiophen-4(5H)one HCl;
6,7-dihydro-5-(((2-hydroxy-3-(2-thienyloxy)cyclopentyl)amino)methyl)-2-methylbenzo(b)thiophen-4(5H)one HCl;
6,7-dihydro-5-(((2-hydroxy-3-(3-thienyloxy)cyclopentyl)amino)methyl)-2-methylbenzo(b)thiophen-4(5H)one HCl;
6,7-dihydro-5-(((2-hydroxy-3-(4-sulfonamidophenoxy)cyclopentyl)amino)methyl)-2-methylbenzo(b)thiophen-4(5H)one HCl;
6,7-dihydro-5-(((2-hydroxy-3-(3-methylsulfonamidophenoxy)cyclopentyl)amino)methyl)-2-methylbenzo(b)thiophen-4(5H)one HCl;
6,7-dihydro-5-(((2-hydroxy-3-(4-pyridinyloxy)cyclopentyl)amino)methyl)-2-methylbenzo(b)thiophen-4(5H)one HCl;
6,7-dihydro-5-(((2-hydroxy-3-(2-methoxyphenoxy)cyclopentyl)amino)methyl)-2-methylbenzo(b)thiophen-4(5H)one HCl;
6,7-dihydro-5-(((2-hydroxy-3-(3-methylphenoxy)cyclopentyl)amino)methyl)-2-methylbenzo(b)thiophen-4(5H)one HCl;
6,7-dihydro-5-(((2-hydroxy-3-(4-methylphenoxy)cyclopenthyl)amino)methyl)-2-methylbenzo(b)thiophen-4(5H)one HCl;
6,7-dihydro-5-(((2-hydroxy-3-(4-methoxyphenoxy)cyclopentyl)amino)methyl)-2-methylbenzo(b)thiophen-4(5H)one HCl;
6,7-dihydro-5-(((2-hydroxy-3-(4-chlorophenoxy)cyclopentyl)amino)methyl)-2-methylbenzo(b)thiophen-4(5H)one HCl;
6,7-dihydro-5-(((2-hydroxy-3-(3,4-dimethoxyphenoxy)cyclopentyl)amino)methyl)-2-methylbenzo(b)thiophen-4(5H)one HCl;
6,7-dihydro-5-(((2-hydroxy-3-(2-fluorophenoxy)cyclopentyl)amino)methyl)-2-methylbenzo(b)thiophen-4(5H)one HCl;
6,7-dihydro-5-(((2-hydroxy-3-(2,3-dimethylphenoxy)cyclopentyl)amino)methyl)-2-methylbenzo(b)thiophen-4(5H)one HCl;
6,7-dihydro-5-(((2-hydroxy-3-(2-ethylphenoxy)cyclopentyl)amino)methyl)-2-methylbenzo(b)thiophen-4(5H)one HCl;
6,7-dihydro-5-(((2-hydroxy-3-(2-methyl-4-chlorophenoxy)cyclopentyl)amino)methyl)-2-methylbenzo(b)thiophen-4(5H)-one HCl;
6,7-dihydro-5-(((2-hydroxy-3-(4-nitrophenoxy)cyclopentyl)amino)methyl)-2-methylbenzo(b)thiophen-4(5H)one HCl;
6,7-dihydro-5-(((2-hydroxy-3-(4-cyanophenoxy)cyclopentyl)amino)methyl)-2-methylbenzo(b)thiophen-4(5H)one HCl;
6,7-dihydro-5-(((2-hydroxy-3-(4-hydroxyphenoxy)cyclopentyl)amino)methyl)-2-methylbenzo(b)thiophen-4(5H)one HCl;
6,7-dihydro-5-(((2-hydroxy-3-(4-trifluoromethylphenoxy)cyclopentyl)amino)methyl)-2-methylbenzo(b)thiophen-4(5H)-one HCl;
6,7-dihydro-5-(((2-hydroxy-3-(4-fluoromethoxyphenoxy)cyclopentyl)amino)methyl)-2-methylbenzo(b)thiophen-4(5H)-one HCl;
6,7-dihydro-5-(((2-hydroxy-3-(4-acetylphenoxy)cyclopentyl)amino)methyl)-2-methylbenzo(b)thiophen-4(5H)one HCl;
6,7-dihydro-5-(((2-hydroxy-3-(4-methylthiophenoxy)cyclopentyl)amino)methyl)-2-methylbenzo(b)thiophen-4(5H)one HCl;
6,7-dihydro-5-(((2-hydroxy-3-(4-carboxyphenoxy)cyclopentyl)amino)methyl)-2-methylbenzo(b)thiophen-4(5H)one HCl;

and the 2,3-dimethylbenzo, 2-methoxybenzo, 2,3-dimethoxybenzo analogs thereof.

EXAMPLE 15

(1α,2β,3β)-6,7-Dihydro-5-(((2-hydroxy-3-phenoxycyclopentyl)amino)methyl)-2-methylbenzo(b)furan-4(5H)one hydrochloride (1α,2α,5β)-2-amino-5-phenoxycyclopentanol (50.0 g) and the furanone of Example 7 were combined in 900 ml EtOH (heat required to dissolve the amine). The cloudy solution was then filtered through celite and the filtrate was allowed to stand at RT° for 3 days (yellow, clear solution). The solution was acidified with ethanolic HCl and refrigerated overnight. The total volume of the solution was reduced to ~500 ml by boiling off EtOH (color of solution went from dark yellow to dark brown). The mixture was then refrigerated for ~4 hours. At this time colorless solid was filtered out, washed with cold EtOH and dried (~40 g). The filtrate was reduced in total volume by ~½ via evaporation of solvent at RT° under a stream of N₂, then refrigerated overnight.

Colorless solid was filtered out, washed with cold EtOH, dried, and combined with the first crop of white solid (~10 g). The filtrate was conc'd in vacuo and diluted with ~200 ml EtOAc. Enough EtOH was added to the near-boiling mixture to effect complete solution and the solution was chilled in an ice/water bath for ~3 hrs. At this time, a third crop of colorless solid was filtered and dried, then combined with the first two crops (~10 g). The filtrate was conc'd in vacuo and the pot residue was partitioned between CH₂Cl₂ and aq. K₂CO₃. The organic layer was washed with H₂0 and dried over NaSO₄ then conc'd in vacuo to an amber oil (~35 g). This oil was flash chromotographed on a silica gel column using 5% McOH in CH₂Cl₂ (trace NH₄OH) as solvent. All fractions containing exclusively the desired product were combined, and concentrated in vacuo to an amber oil. This oil was diluted with ~200 ml EtOH, acidified with ethanolic HCl, and refrigerated for 3 days to yield the desired product.

In a similar manner by changing the 2-aminocyclopentanol reactant of the foregoing example with the isomeric forms of the listed compounds of following Example 4 and by substantially following the procedure of this example there are produced the (1α,2α,3β), (1β,2α,3β), (1α,2β,3β) and (1β,2β,3β) isomeric forms of the 6,7-dihydro-5-(((2-hydroxy-3-aryloxycyclopentyl)amino)methyl)-2-methylbenzo(b)furan-4(5H)one analogs of those 6,7-dihydro-5-(((2-hydroxy-3-aryloxycyclopentyl)amino)methyl)-2-methylbenzo(b)thiophen-4(5H)one listed compounds following Example 14.

EXAMPLE 16

(1β,2α,3β)-6,7-Dihydro-5(((2-hydroxy-3-phenoxycyclohexyl)amino)methyl)-2-methylbenzo(b)-thiophen-4-(5H)-one (1α,2β,6β)-2-amino-6-phenoxycyclohexanol (2.0 g) and the methylene ketone of Example 6 (2.1 g) were admixed in round bottom flask to which was added Et$_2$O (20 ml) followed by 15 ml methanol in 1 ml portions. The mixture was stirred for 72 hours at room temperature under N$_2$. With stirring another 2 gm of methylene ketone plus 1 drop 5N.HCl was added and the mixture stirred overnight. Material is concentrated (but not to dryness) and cooled. The solids are filtered off, and the solution concentrated to dryness. The product is recrystallized from acetonitrile to yield the desired product.

EXAMPLE 17

(1β,2β,3α)-6,7-Dihydro-5-(((2-Hydroxy-3-Phenoxycyclobutyl)amino)methyl)-2-methylbenzo(b)thiophen-4(5H)-one The free amine of Example 5 is dissolved in ethanol (1 mol. conc) and treated with a 1 molar ethanolic solv. of the exocyclic ketone of Example 6 and the mixture is allowed to stand at room temperature for 6 hours and is then cooled to −20° C. overnight. The resulting white crystals are collected by filtration and the desired product is converted to its hydrochloride salt by treatment with ethanolic HCl.

EXAMPLE 18

(1α,2α,3β)-2(((2-Hydroxy-3-Phenoxycyclopentyl)amino)methyl)-1-tetralone

Combine (1α,2α,5β)-2-amino-5-phenoxy cyclopentanol (0.97 g) and 2-methylene-1-tetralone (1.2 g) in 20 ml ethanol and let stand at room temperature for 24 hours. Acidify the mixture with ethanolic hydrochloride and the resultant solution is gently concentrated in vacuo. The residue is triturated with a cold mixture of 2:1:1 EtOH. Acetone: Et$_2$O to yield the desired product as a white powder, mp. 162°–164° C.

EXAMPLE 19

(1α,2α,3β)-6,7-Dihydro-5-(((2-hydroxy-3-phenoxycyclopentyl)amino)methyl)-2-methylbenzo(b)thiophen-4(5H)-ol Hydrochloride To an ethanolic solution (100 ml) of the amine hydrochloride of Example 11 (5.85 g, 0.014 mol) was added 4.6 g of NaBH$_4$ (gas evolution). After 2 hr, water (100 ml) was added dropwise to the reaction, followed by the dropwise addition of 3 ml of HOAc (gas evolution). The quenched reaction was diluted with an equal volume of sat'd. NaCl and extracted with EtOAc (2×400 ml). The extracts were dried (Na$_2$SO$_4$), filtered and concentrated (rotovap) to afford 4.55 g of crude aminodiol. The crude product was chromatographed on a 600-g column of silica gel 60 (70–230 mesh, 5×73 cm) which was packed and eluted with chloroform-methanol (95:5) (2L), then with chloroform methanol (90:10). Fractions were collected (10×200 ml, then 75–100 ml each) and examined by TLC (SS1). Fractions containing the desired aminodiol were combined and concentrated (rotovap) to afford 1.3 g of product which was evacuated to a foam and triturated with either. Vacuum filtration and drying furnished 0.4 g (1.07 mmol) of the desired aminodiol product, mp 190°–192° C. A 0.70 g (1.87 mol) portion of the aminodiol was dissolved in warm CH$_3$CN—CH$_3$OH (1:1, 35 ml) and the amber solution was filtered. To the filtrate was added 1.9 ml (1.9 mmol) of 1N HCl and the solution was concentrated under a nitrogen stream. The crystals which were obtained were vacuum filtered and air-dried. The crystals were recrystallized from EtOH-Et$_2$O and dried (vacuum) to obtain 0.4 g (0.976 mmol) of the hydrochloride, mp. 223°–224.5° C. dec.

In a similar manner by following the techniques of this example, the other compounds enhanced by Formula I may also chemically be reduced.

Having described the methods for preparing the compounds of this invention, the manner of using the invention sought to be patented is described as follows.

The compounds of Formula I possess the ability to exert potent blood pressure lowering effects in mammals having hypertension. Although the mechanism by which this occurs has not yet been completely identified, it is clear that arterial blood pressure decreases, at least in part, as a result of peripheral vasodilation. In effecting their anti-hypertensive effects in mammals the incidence of the usual side effects associated with other synthetic drugs of this class is limited and thus, considering the problems associated with these currently available antihypertensives, the compounds of this invention have a very favorable pharmacological profile. Indeed, by virtue of the pharmacological profile the compounds of this invention may be administered without the need for conjunctive therapy with diuretics or beta blockers and, in view of the increase in renal blood flow may also be useful in the treatment of renal failure, and additionally the compounds may also be useful in the treatment of congestive heart failure.

Utilizing standard laboratory tests, such as, for example, the Spontaneously Hypertensive Rat (SHR) assay for determining antihypertensive activity, and standard techniques using phenylephrine as the agonist in anesthetized dogs for determining alpha-adrenergic receptor blocking activity, as well as other standard laboratory tests, the pharmacological profile of the compounds of this invention may be studied. From standard tests the compounds of this invention exhibit antihypertensive effects in mammals at a dose range of 1–30 MPK orally in the rat and 0.1–10 MPK orally in the dog. Therefore, based upon these and other standard laboratory methodology for determining end-use application, as well as by comparison with known agents having the aforementioned end-use applications, it is expected that the compounds will be effective at a dose range of about 0.1 to 10 MPK per day in man. Quite naturally the specific dosage will depend upon the severity and nature of the disease state, the age and general condition of the patient as well as the method by which the active ingredient will be administered, all of which is determined by the attending diagnostician by techniques well known in the art.

The preferred route of administration is via oral administration. Illustrative dosage levels of the active ingredient for oral administration range from 0.1 to 10 MPK, preferably from 1 to 2.5 MPK per day with corresponding lower doses when the active ingredient is via the parenteral route.

Formulations for oral use may be presented as hard or soft shelled gelatin capsules containing only the active ingredient, but generally blended with conventional pharmaceutical carriers or excipients such as gelatin, various starches, lactose, calcium phosphate, or powdered sugar. The term pharmaceutical carrier is intended to include lubricants employed to improve the flow of tablet granulations and to prevent the adhesion of tablet material to the surfaces of tablet dies and punches. Suitable lubricants include, for example, talc, stearic acid, calcium stearate, magnesium stearate and zinc stearate. Also included in the definition of a pharmaceutical carrier as used herein are disintegrating agents added to assist the break up and dissolution of tablets following administration, dyes and coloring agents, and flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients include water, saline solution, dextrose and glycol solution, as for example an aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil, and soybean oil. Where a compound is insoluble in the particular vehicle chosen, suspending agents may be added as well as agents to control viscosity of the solution, as for example, magnesium aluminum silicate or carboxymethylcellulose. In addition to these excipients, buffers, preservatives and emulsifying agents may also be suitably employed.

The proportion of the active ingredient employed in parenteral dosage unit forms ranges from about 0.05 to about 20% by weight, preferably from about 0.1 to about 10% by weight of the total liquid composition, the remaining component or components comprising any of the various pharmaceutical excipients previously disclosed. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more surfactants use in parenteral formulations are the class of polyoxyethylene sorbitan fatty acid esters as for example, sorbitan monooleate and the high molecular weight adducts of ethylene oxide with a hydrophobic base, formed by the condensation of propylene oxide with propylene glycol.

The following examples illustrate pharmaceutical preparations suitable for use with the compounds of this invention. In these examples the active ingredient is the compound of Example 11, i.e., (1α,2α,3β)-6,7-dihydro-5-(((2-hydroxy-3-phenoxycyclopentyl)amino)methyl)-2-methylbenzo(b)thiophene-4(5H)-one HCl.

TABLET FORMULATION

The following formulation provides for the manufacture of 1,000 tablets.

|  | Grams |
| --- | --- |
| (1) Active Ingredient | 25 |
| (2) Lactose, USP | 181 |
| (3) Corn Starch, USP | 92.5 |
| (4) Magnesium Stearate | 1.5 |

Thoroughly granulate a mixture of 92.5 g of corn starch and the lactose with a paste prepared by dissolving 20 gms of corn starch in 100 ml of hot distilled water. Dry the resulting granulation at 40°–45° C. and pass it through a No. 16 mesh screen. To the dried, screened granulation add a blended mixture of the active ingredient (1) and the magnesium stearate. Thoroughly blend and then press into tablets of 500 mg each.

CAPSULE FORMULATION

The following formulation provides for the manufacture of 1,000 capsules:

|  | Grams |
| --- | --- |
| (1) Active Ingredient | 25 |
| (2) Lactose | 271.5 |
| (3) Magnesium stearate | 1.5 |

Mix active ingredient (1) with the lactose and blend in the magnesium stearate. Fill hard gelatin capsules with 300 mg each of the blended mixture to produce capsules containing 25 mg of active ingredient.

PARENTERAL FORMULATION

The following formulation provides for the manufacture of 1,000 vials each containing 10 mg of active ingredient.

|  | Grams |
| --- | --- |
| (1) Active ingredient | 10.0 |
| (2) Monobasic potassium phosphate | 6.0 |
| (3) Water for injection USP qs liter | 1.0 |

Dissolve ingredients (1), (2), and (3) in approximately 80 percent of the volume of water and filter the resulting solution. Add to the filtrate sufficient water to make to a 1000 ml volume. Sterile-filter the solution and asceptically fill one milliliter portions of the so-prepared solution into two milliliter vials, then lyophylize. After the lyophilized cake is dry, aseptically stopper the vials with rubber plugs and seal.

As is true for most large classes of compounds suitable for therapeutic application in the treatment of hypertension certain sub-classes and specific compounds are preferred. Insofar as the compounds of the instant application are concerned, the preferred compounds are those wherein "B" together with the carbon atoms to which it is attached form a cyclopentanol moiety. Preferred compounds are those wherein "Q" represents a methylene moiety. Preferred compounds are those wherein the aryl (Ar) moiety is phenyl, thienyl or indole with phenyl being most preferred. Preferred substituents on the aryl moieties are methyl, methoxy, sulfonamido, methylsulfonamido, chloro and dimethyl. The preferred stereoisomers are those having the 1α,2α,3β (i.e., cis-trans) and the 1α,2β,3β (i.e., trans-cis) configurations. Most preferred configurations are those stereoisomeric forms wherein the aryloxy and the amine moieties attached to the cyclopentanol moiety are trans to each other, particularly when the hydroxy substituent of the cyclopentanol is alpha. The most preferred are those compounds wherein "Ar" represents phenyl, "B" represents ethylene, "Q" represents methylene, and "X" represents sulfur, oxygen or NR. Most preferred compounds are 6,7-dihydro-5-(((2-hydroxy-3-phenoxycyclopentyl)amino)methyl)-2-methylbenzo(b)thiophen-4(5H)-one, 6,7-dihydro-5-(((2-hydroxy-3-(indoloxy)cyclopentylamino)methyl)-2-methylbenzo(b)thiophen-4(5H)-one, 6,7-dihydro-5-(((2-hydroxy-3-(2-methylphenoxy)cyclopentyl)amino)methyl)-2-methylbenzo(b)thiophen-4(5H)-one, 6,7-dihydro-5-(((2-hydroxy-3-(4-chloro-2-methylphenoxy)cyclopentyl)amino)methyl)-2-methylbenzo(b)thiophen-4(5H)-one, 6,7-dihydro-5-(((2-hydroxy-3-(3-methylsulfonamidophenoxy)cyclopentyl)amino)methyl)-2-methylbenzo(b)thiophen-4(5H)-one, 6,7-dihydro-5-(((2-hydroxy-3-(4-sulfonamidophenoxy)cyclopentyl)amino)methyl)-2-methylbenzo(b)thiophen-4(5H)-one, 6,7-dihydro-5-(((2-hydroxy-3-thienyloxycyclopentyl)amino)methyl)-2-methylbenzo(b)thiophen-4(5H)-one, and the corresponding 2-methylbenzo(b)furan-4(5H)-ones, the 2-methyl-1H-indol-4(5H)-ones; each one of the preceding 21 compounds being in any of the aforementioned stereoisomeric configurations.

We claim:

1. A compound of the structural formula

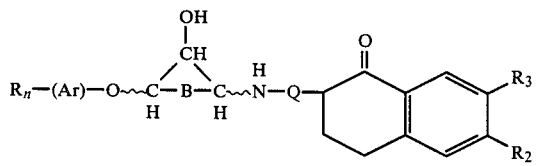

and the pharmaceutically acceptable salts thereof, wherein Ar represents phenyl, naphthyl, indolyl, thienyl or pyridyl; the R represents hydrogen, lower alkyl, halogeno, nitro, trifluoromethyl, trifluoromethoxy, methylenedioxy, lower alkanoyl, carboxy, hydroxy, lower alkoxy, cyano, —SO$_2$NH$_2$, lower alkylthio, CH$_3$SO$_2$NH—, amino, carboxamido, amidino or imidazol-2-yl; n represents 1, 2 or 3, B or Q each represent an alkylene bridge having 1 to 3 carbon atoms; with R$_2$ and R$_3$ each being hydrogen, lower alkyl, lower alkyl or phenyl.

2. A compound having the structural formula

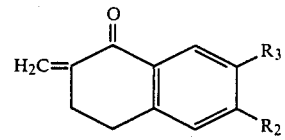

wherein R$_2$ and R$_3$ are as defined in claim 1.

3. A compound of claim 1 wherein B is ethylene.

4. A compound of claim 3 wherein Q is methylene.

5. A compound of claim 4 wherein Ar is phenyl.

6. A compound of claim 3, wherein relative to each other the aryloxy and the amino moieties attached to the cyclopentanol moiety are in the trans stereoisomeric configuration.

7. A method for the treatment of hypertension in a patient having hypertension which comprises administering a compound of claim 1.

8. A compound of claim 7 wherein each of R$_2$ and R$_3$ are hydrogen, said compound being 2-methylene-1-tetralone.

9. A compound of claim 8 wherein R$_2$ is 6-methyl and R$_3$ is hydrogen, said compound being 2-methylene-6-methyl-1-tetralone.

10. A compound of claim 9 wherein R$_2$ and R$_3$ each are methyl, said compound being 6,7-dimethyl-2-methylene-1-tetralone.

11. A compound of claim 10 wherein R$_2$ is 6-methoxy, R$_3$ is 7-methoxy, said compound being 6,7-dimethoxy-2-methylene-1-tetralone.

12. A compound of claim 11 wherein R$_2$ is 6-phenyl and R$_3$ is hydrogen, said compound being 2-methylene-6-phenyl-1-tetralone.

13. A compound of claim 12, said compound being 2-(((2-hydroxy-3-phenoxycyclopentyl)amino)methyl)-1-tetralone, said compound being any of its (1α, 2α, 3β), (1β, 2α, 3β), (1α, 2β, 3β) and (1β, 2β, 3β) stereoisomeric configurations, and their enantiomers.

14. A compound of claim 13, said compound being 2-(((2-hydroxy-3-phenoxycyclopentyl)amino)methyl)-6-methyl-1-tetralone, said compound being in any of its (1α, 2α, 3β), (1β, 2α, 3β), (1α, 2β, 3β) and (1β, 2β, 3β) stereoisomeric configurations, and their enantiomers.

15. A compound of claim 14, said compound being 2-(((2-hydroxy-3-phenoxycyclopentyl)amino)methyl)-6,7-dimethyl-1-tetralone, said compound being in any of its (1α, 2α, 3β), (1β, 2α, 3β), (1α, 2β, 3β) and (1β, 2β, 3β) stereoisomeric configurations, and their enantiomers.

16. A compound of claim 15, said compound being 2-(((2-hydroxy-3-phenoxycyclopentyl)amino)methyl)-6,7-dimethoxy-1-tetralone, said compound being in any of its (1α, 2α, 3β), (1β, 2α, 3β), (1α, 2β, 3β) and (1β, 2β, 3β) stereoisomeric configurations, and their enantiomers.

17. A compound of claim 16, said compound being 2-(((2-hydroxy-3-phenoxycyclopentyl)amino)methyl)-6-phenyl-1-tetralone, said compound being in any of its (1α, 2α, 3β), (1β, 2α, 3β), (1α, 2β, 3β) and (1β, 2β, 3β) stereoisomeric configurations, and their enantiomers.

* * * * *